US010295536B2

United States Patent
Boone et al.

(10) Patent No.: US 10,295,536 B2
(45) Date of Patent: *May 21, 2019

(54) **FECAL LACTOFERRIN AS A BIOMARKER FOR DETERMINING DISEASE SEVERITY AND FOR TREATING INFECTION IN PATIENTS WITH *CLOSTRIDIUM DIFFICILE* DISEASE**

(71) Applicant: TECHLAB, INC., Blacksburg, VA (US)

(72) Inventors: James Hunter Boone, Christianburg, VA (US); David M. Lyerly, Radford, VA (US); Tracy D. Wilkins, Riner, VA (US); Robert J. Carman, Christianburg, VA (US)

(73) Assignee: TECHLAB, INC., Blacksburg, VA (US)

(*) Notice: Subject to any disclaimer, the term of this patent is extended or adjusted under 35 U.S.C. 154(b) by 207 days.

This patent is subject to a terminal disclaimer.

(21) Appl. No.: 14/249,814

(22) Filed: Apr. 10, 2014

(65) Prior Publication Data

US 2014/0219966 A1 Aug. 7, 2014

Related U.S. Application Data

(62) Division of application No. 13/457,064, filed on Apr. 26, 2012, now abandoned.

(Continued)

(51) Int. Cl.
*G01N 33/569* (2006.01)
*A61K 35/74* (2015.01)
(Continued)

(52) U.S. Cl.
CPC .... *G01N 33/56911* (2013.01); *A61K 31/4164* (2013.01); *A61K 31/7034* (2013.01);
(Continued)

(58) Field of Classification Search
None
See application file for complete search history.

(56) References Cited

U.S. PATENT DOCUMENTS 7,192,724 B2 3/2007 Boone et al.
2008/0096189 A1 4/2008 Boone et al.
(Continued)

FOREIGN PATENT DOCUMENTS

JP 2000155121 A 6/2000
JP 2008522165 A 6/2008
(Continued)

OTHER PUBLICATIONS

Steiner et al., Clinical and Diagnostic Laboratory Immunology, 4(6):719-722, 1997.*

(Continued)

*Primary Examiner* — Jennifer Pitrak McDonald
*Assistant Examiner* — Qing Xu
(74) *Attorney, Agent, or Firm* — Shook, Hardy & Bacon L.L.P.

(57) ABSTRACT

*Clostridium difficile* disease involves a range of clinical presentations ranging from mild to self-limiting diarrhea to life-threatening pseudomembranous colitis and megacolon. Cases of *C. difficile* are treated differently depending on severity of disease. Mild and moderate cases may be treated with metronidazole while moderate-to-severe and relapsing cases are often treated with vancomycin or fidaxomicin. The presence of *C. difficile* disease is detected using a biomarker panel that includes *C. difficile* antigen (GDH), toxins A and B, and fecal lactoferrin. In patients suspected of *C. difficile* disease, if GDH is detected indicating the presence of *C. difficile*, and then toxins A and/or B are detected to indicate toxigenic *C. difficile* and support a diagnosis of *C. difficile*-associated disease, fecal lactoferrin concentrations are mea- (Continued)

sured to determine severity of the disease by indicating the amount of intestinal inflammation.

8 Claims, 3 Drawing Sheets

Related U.S. Application Data

(60) Provisional application No. 61/480,616, filed on Apr. 29, 2011.

(51) Int. Cl.
    *A61K 45/06*       (2006.01)
    *A61K 38/14*       (2006.01)
    *A61K 31/4164*     (2006.01)
    *A61K 31/7034*     (2006.01)

(52) U.S. Cl.
    CPC .............. *A61K 35/74* (2013.01); *A61K 38/14* (2013.01); *A61K 45/06* (2013.01); *G01N 2333/33* (2013.01); *G01N 2333/79* (2013.01); *G01N 2800/52* (2013.01); *G01N 2800/56* (2013.01)

(56) References Cited

U.S. PATENT DOCUMENTS

| 2009/0253155 | A1 | 10/2009 | Boone et al. |
| 2012/0276059 | A1 | 11/2012 | Boone et al. |
| 2016/0370361 | A1 | 12/2016 | Boone et al. |

FOREIGN PATENT DOCUMENTS

| JP | 2014519018 | A | 8/2014 |
| WO | 9845706 | A1 | 10/1998 |
| WO | 0239883 | A2 | 5/2002 |
| WO | 2009108652 | A1 | 9/2009 |
| WO | 2012149351 | A1 | 11/2012 |

OTHER PUBLICATIONS

Oppenheim et al., Scientific Symposium on New Approaches to Clostridium difficile Testing, Oct. 23-27, 2010. Available online (see IDS filed on Dec. 20, 2013 in the parent case U.S. Appl. No. 13/457,064).*
Guideline, 2008, available online at http://www.cumc.columbia.edu/dept/id/documents/Guidelines-Clostridiumdifficile-8-28-08.pdf.*
Dai et al. Scandinavian Journal of Gastroenterology, 42:1440-1444, 2007.*
McFarland, Journal of Medical Microbiology (2005), 54, 101-111.*
Van Langenberg et al., Internal Medicine Journal, 40: 819-827, 2010.*
Non-Final Office Action dated Mar. 10, 2015 in U.S. Appl. No. 13/664,383, 30 pages.
Vaughn et al. (2006). C. DiffChek™-60: A Rapid and Cost Effective Method for Detection of Clostridium difficile in Fecal Specimens. Poster from the Clinical Virology meeting. Pub. Date from http://www.techlab.com/diagnostics/c-difficile/c-diff-chek60-t5025/.
C Diff Chek™-60 product insert (2011), from Techlab. at http://www.techlab.com/wp-content/uploads/2013/06/t5025insert_rev_0311.pdf.
Eastwood et al. (2009). Comparison of Nine Commercially Available Clostridium difficile Toxin Detection Assays, a Real-Time PCR Assay for C. difficile tcdB, and a Glutamate Dehydrogenase Detection Assay to Cytotoxin Testing and Cytotoxigenic Culture Methods. Journal of Clinical Microbiology, v47(10), p. 3211-3217.
Non-Final Office Action dated May 4, 2015 in U.S. Appl. No. 13/457,049, 36 pages.
Wren et al. (2009a). Laboratory diagnosis of Clostridium difficile infection. An evaluation of tests for faecal toxin, glutamate dehydrogenase, lactoferrin and toxigenic culture in the diagnostic laboratory. British Journal of Biomedical Science. v66(1), p. 1-5.
Wren et al. (2009b).Detection of. Clostridium difficile infection: a suggested laboratory diagnostic algorithm. British Journal of Biomedical Science, v66(4), p. 175-179.
IBD-SCAN product insert, by Tech Lab. 36 pages. Apr. 2008.
European Extended Search Report dated Oct. 15, 2014 in Application No. 12777788.6, 9 pages.
Shen, E.P. et al, Current treatment options for severe Clostridium difficile-associated disease, Gastroenterology & Hepatology, Millennium Medical Publishing, US, vol. 4, No. 2, Feb. 1, 2008, pp. 134-139, XP009148951.
Non-Final Office Action dated Sep. 28, 2016 in U.S. Appl. No. 13/664,383, 28 pages.
Non-Final Office Action dated Sep. 28, 2016 in U.S. Appl. No. 13/457,049, 27 pages.
European Extended Search Report dated Oct. 9, 2015 in Application No. 12838635.6, 12 pages.
L. Fenner et al: "Rapid and Reliable Diagnostic Algorithm for Detection of Clostridium difficile", Journal of Clinical Microbiology, vol. 46, No. 1, Nov. 21, 2007 (Nov. 21, 2007 ), pp. 328-330, XP055216114, ISSN: 0095-1137, DOI: 10.1128/JCM.01503-07.
First Examination Report dated Sep. 9, 2015 in New Zealand Application No. 701004, 3 pages.
Final Office Action dated Oct. 19, 2015 in U.S. Appl. No. 13/644,383, 27 pages.
Final Office Action dated Nov. 2, 2015 in U.S. Appl. No. 13/457,049, 22 pages.
Kelley CP et al. (1994). Clostridium difficile colitis. New England Journal of Medicine, v330(4), p. 257-262.
Steiner TS et al. (1997), Fecal Lactoferrin, interluekin-1beta, and Interluekin-8 are elevated in patients with severe Clostrudum difficule colitis. Clincial and Diagnostic Laboratory Immunology, v4(6), p. 719-722.
Yoon et al. Treatment of Refractory/Recurrent C. difficile-associated Disease by Donated Stool Transplanted via Colonscopy. J Clin Gastroenterol Sep. 2010 vol. 44 No. 8 pp. 562-566. Especially abstract.
New Zealand Office Action dated Apr. 4, 2016 in Application No. 701004, 5 pages.
Kvach et al. "Comparison of BD GeneOhm Cdiff Real-Time PCR Assay with a Two-Step Algorithm and a Toxin A/B Enzyme-Linked Immunosorbent Assay for Diagnosis of Toxigenic Clostridium difficile infection." Journal of Clinical Microbiology (online), Jan. 2010 [Retrieved on 2013-Feb. 2012], vol. 48, No. 1, para 1-3, p. 110, col. 2, para 2-3; p. 111, col. 1, para 3; p. 112, col. 1, para 3; p. 112, col. 1, para 3.
Michael T. Kelly, Commercial Latex Agglutination Test for Detection of Clostridium Difficile-Associated Diarrhea, Journal of Clinical Microbiology, 1987, vol. 25, No. 7, pp. 1244-1247.
David M. Lyerly, Identification of the Latex Test-Reactive Protein of Clostridium Difficile as Glutamate Dehydrogenase, Journal of Clinical Microbiology, 1991, vol. 29, No. 11, pp. 2639-2642.
David M. Lyerly, Commercial Latex Test for Clostridium Difficile Toxin A Does Not Detect Toxin A, Journal of Clinical Microbiology, 1986, vol. 23, No. 3, pp. 622-623.
Canadian Office Action dated Jul. 13, 2016 for Canadian Patent Application No. 2871613, 4 Pages.
Final Office Action dated Jun. 27, 2017 in U.S. Appl. No. 13/457,049, 25 pages.
Non-Final Office Action dated Jun. 27, 2017 in U.S. Appl. No. 13/664,383, 31 pages.
Translated Japanese Office Action dated Jan. 4, 2017 in Japanese Patent Application No. 2015-508933, 4 pages.
Shetty N, The Role of Glutamate Dehydrogenase for the Detection of Clostridium Difficile in Faecal Samples: A Meta-Analysis, J Hosp Infect, 2011, vol. 47, NR: 10, pp. 3211-3217.
Kelly W F, Evaluation of the latex agglutination test for detection of Clostridium difficile, Archives of pathology & laboratory medicine, 1992,vol. 116, No. 5, p. 517-520.
C. Diff Check-60 T5025, An enzyme immunoassay for the detection of glutamate dehydrogenase (GDH) produced by both toxigenic and

(56) References Cited

OTHER PUBLICATIONS non-toxigenic strains of Clostridium difficile, Dec. 16, 2016, URL,http://www.techlab.com/diagnostics/c-difficile/c-diff-chek-60-t5025.
Office Action dated Apr. 7, 2017 in European Patent Application No. 12838635.6, 8 pages.
Canadian Office Action dated Apr. 18, 2017 for Canadian Patent Application No. 2,871,613, 4 pages.
Examination Report dated Dec. 22, 2017 in Australian Patent Application No. 2012318345, 3 pages.

* cited by examiner

FIG. 4A

| N=9 ID | AGE (YR) | SEX M/F | T=0 LAC (µg/g) | T=0 GDH | T=0 ABII | T=0 SPORE COUNTS | T=0 PCR RIBOTYPE | FIRST FOLLOW-UP LAC (µg/g) | FIRST FOLLOW-UP GDH | FIRST FOLLOW-UP ABII | FIRST FOLLOW-UP SPORE COUNTS | FIRST FOLLOW-UP PCR RIBOTYPE |
|---|---|---|---|---|---|---|---|---|---|---|---|---|
| 3 | 76 | F | 448 | 4.144 | 3.986 | 1.80E+04 | ARL 251 | 0 | 0 | 0 | 0 | N/A |
| 4 | 78 | M | 44 | 4.342 | 4.126 | 5.00E+04 | ARL 305 | 22 | 0 | 0 | 0 | N/A |
| 5 | 65 | F | 13 | 4.197 | 4.054 | 4.00E+05 | ARL 005 | 18 | 0 | 0 | 0 | N/A |
| 7 | 53 | M | 406 | 4.307 | 3.938 | 1.60E+04 | ARL 027 | 0 | 0 | 0 | 0 | N/A |
| 11 | 24 | F | 151 | 4.101 | 0.556 | 7.00E+02 | ARL 001 | 1 | 0 | 0 | 0 | N/A |
| 12 | 55 | M | 14 | 4.487 | 1.787 | 4.00E+02 | ARL 027 | 12 | 0 | 0 | 0 | N/A |
| 14 | 79 | F | 515 | 4.327 | 3.889 | 3.50E+05 | ARL 054 | 4 | 0 | 0 | 0 | N/A |
| 17 | 77 | F | 1291 | 4.304 | 4.215 | 8.00E+03 | ARL 059 | 2 | 0 | 0 | 0 | N/A |
| 19 | 72 | F | 1826 | 4.125 | 4.110 | 4.50E+05 | ARL 027 | 72 | 0.098 | 0 | 0 | N/A |
| MEDIAN | 72 | | 406 | 4.304 | 3.986 | 1.80E+04 | 33% 027 | 4 | 0 | 0 | 0 | |

FIG. 4B

| N=5 ID | AGE (YR) | SEX M/F | T=0 LAC (µg/g) | T=0 GDH | T=0 ABII | T=0 SPORE COUNTS | T=0 PCR RIBOTYPE | FIRST FOLLOW-UP LAC (µg/g) | FIRST FOLLOW-UP GDH | FIRST FOLLOW-UP ABII | FIRST FOLLOW-UP SPORE COUNTS | FIRST FOLLOW-UP PCR RIBOTYPE |
|---|---|---|---|---|---|---|---|---|---|---|---|---|
| 2 | 80 | F | 73 | 4.180 | 3.130 | 3.20E+03 | ARL 027 | 17 | 5.000 | 0.478 | 4.00E+03 | ARL 027 |
| 8 | 35 | M | 403 | 4.225 | 4.097 | 1.30E+05 | ARL 027 | 0 | 0.633 | 0.943 | 5.80E+03 | ARL 027 |
| 10 | 79 | F | 10 | 0.038 | 0 | 3.00E+04 | ARL 014 | 2 | 0 | 0 | 1.00E+02 | ARL 027 |
| 15 | 82 | F | 85 | 4.434 | 3.696 | 5.00+03 | ARL 126 | 57 | 0 | 0 | 1.00E+02 | ARL 126 |
| 16 | 49 | F | 164 | 5 | 1.512 | 1.90E+05 | ARL 056 | 0.4 | 4.151 | 0 | 4.20E+04 | ARL 379 |
| MEDIAN | 79 | | 85 | 4.225 | 3.130 | 3.00E+04 | 40% 027 * | 2 | 0.633 | 0 | 4.00E+03 | 60% 027 |

FIG. 4C

| N=4 ID | AGE (YR) | SEX M/F | T=0 LAC (µg/g) | T=0 GDH | T=0 ABII | T=0 SPORE COUNTS | T=0 PCR RIBOTYPE | FIRST FOLLOW-UP LAC (µg/g) | FIRST FOLLOW-UP GDH | FIRST FOLLOW-UP ABII | FIRST FOLLOW-UP SPORE COUNTS | FIRST FOLLOW-UP PCR RIBOTYPE |
|---|---|---|---|---|---|---|---|---|---|---|---|---|
| 1 | 59 | F | 11 | 4.192 | 0.884 | 6.20E+04 | ARL 054 | 433 | 3.89 | 1.442 | 1.00E+05 | ARL 103 |
| 18 | 75 | M | 423 | 5.000 | 4.293 | 1.50E+05 | ARL 126 | 196 | 3.977 | 0.798 | 4.40E+04 | ARL 126 |
| 9 | 75 | F | 301 | 4.225 | 4.076 | 1.50E+05 | ARL 005 | 135 | 4.153 | 3.691 | 2.80E+04 | ARL 027 |
| 20 | 86 | F | 1541 | 4.503 | 2.299 | 1.00E+04 | ARL 126 | 2155 | 4.157 | 3.909 | 2.80E+04 | ARL 126 |
| MEDIAN | 75 | | 362 | 4.364 | 3.188 | 1.06E+05 | NO 027  | 315 | 4.065 | 2.567 | 3.60E+04 | 25% 027** |

FECAL LACTOFERRIN AS A BIOMARKER FOR DETERMINING DISEASE SEVERITY AND FOR TREATING INFECTION IN PATIENTS WITH *CLOSTRIDIUM DIFFICILE* DISEASE

CROSS-REFERENCE TO RELATED APPLICATIONS

This application is a divisional application of pending U.S. patent application Ser. No. 13/457,064, filed Apr. 26, 2012, entitled "Fecal Lactoferrin as a Biomarker for Determining Disease Severity and for Monitoring Infection in Patients with *Clostridium Difficile* Disease," which claims priority to U.S. Provisional Patent Application No. 61/480,616, filed Apr. 29, 2011, entitled "Fecal Lactoferrin as a Biomarker for Determining Disease Severity and for Monitoring Infection in Patients with *Clostridium Difficile* Disease," both of which are herein incorporated by reference.

BACKGROUND

*Clostridium difficile* infection (CDI) involves a range of clinical presentations including mild to self-limiting diarrhea to life-threatening pseudomembranous colitis and megacolon. Many healthy persons (e.g., infants) carry *Clostridium difficile* (*C. difficile*), and many patients become asymptomatic carriers after admission to the hospital. Most cases are diagnosed based on clinical evaluations, history of antibiotic use, and the presence of the organism and/or toxins A & B (i.e., TcdA and TcdB, respectively) in the stool. Enzyme-linked immunoassay (EIA) tests are the most frequently used test format for measuring toxin in the stool specimens, with tissue culture combined with specific neutralization being the gold standard for detecting stool toxin. More recently, polymerase chain reaction (PCR) tests are available for determining the presence of *C. difficile* toxin A and B genes (tcdA and tcdB) and these are used as stand-alone tests and in combination with the detection of glutamate dehydrogenase (GDH) for ruling out *C. difficile*-negative patients. All of these assays are suitable for detecting the presence of *C. difficile* as an aid to diagnosis but do not provide information about the severity of disease.

The severity of the disease is an important factor to recommending a proper course of treatment. In general, patients with *C. difficile* disease often present with fever, have slightly raised white blood cells (leukocytosis) and experience mild abdominal pain. Mild cases respond well to stopping the inciting antibiotic while moderate and/or moderate-to-severe *C. difficile* disease cases often require antibiotic intervention. Currently, no single lab parameter is routinely used to stratify patients based on severity of CDAD for optimizing medical and/or surgical treatment.

BRIEF DESCRIPTION OF SEVERAL VIEWS OF THE DRAWINGS

Illustrative embodiments of the invention are described in detail below with reference to the attached drawing figures, wherein:

FIG. 4A depicts a summary of biomarker results for nine patients (N=9) with a clinical cure (no symptoms and no *C. difficile* during and/or after initial treatment) where the biomarkers were determined at the time of admission (T=0) and at a first follow-up, and where the biomarkers tested include lactoferrin levels (denoted LAC) in μg/g, glutamate dehydrogenase (denoted GDH), toxin A and toxin B (denoted ABII), spore counts, and PCR ribotype according to embodiments of the invention;

FIG. 4B depicts a summary of biomarker results for five patients (N=5) with bacterial reinfection (return of *C. difficile* in absence of symptoms during and /or after initial treatment) where the biomarkers were determined at the time of admission (T=0) and at a first follow-up, and where the biomarkers tested include lactoferrin levels (denoted LAC) in μg/g, glutamate dehydrogenase (denoted GDH), toxin A and toxin B (denoted ABII), spore counts, and PCR ribotype according to embodiments of the invention; and FIG. 4C depicts a summary of biomarker results for four patients (N=4) with clinical recurrence or no cure (return of symptoms and *C. difficile* during and /or after initial treatment) where the biomarkers were determined at the time of admission (T=0) and at a first follow-up, and where the biomarkers tested include lactoferrin levels (denoted LAC) in μg/g, glutamate dehydrogenase (denoted GDH), toxin A and toxin B (denoted ABII), spore counts, and PCR ribotype according to embodiments of the invention.

DETAILED DESCRIPTION

Figure 1:
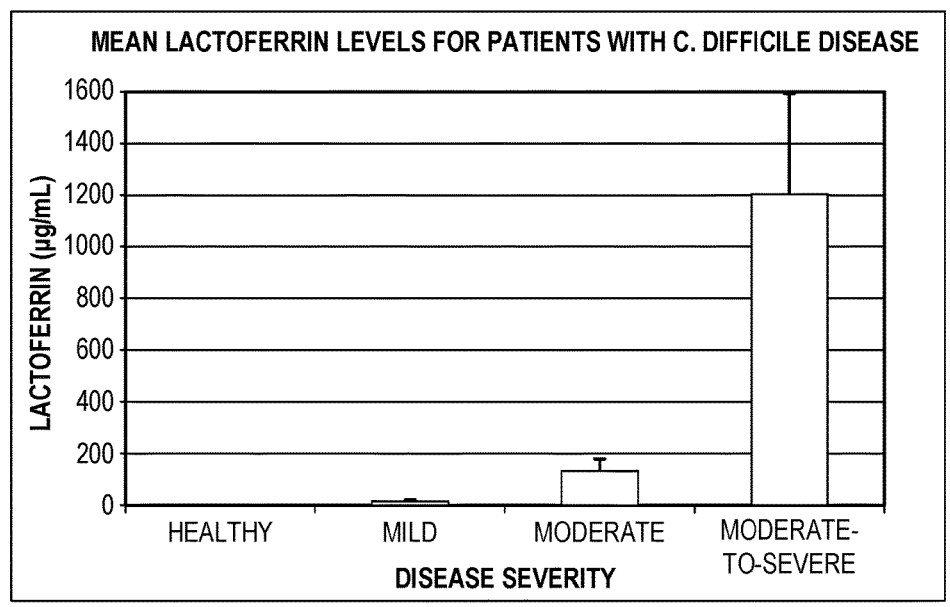
FIG. 1 depicts mean lactoferrin levels (μg/mL±standard error) for patients with clinically defined cases of *C. difficile* disease stratified by severity according to embodiments of the invention.

The present invention is directed to test methods for aiding in stratifying patients based on severity of *C. difficile* disease. Stratifying patients with disease based on severity using a panel of biomarkers is a new concept that is critically needed because of the increase in incidence and frequent severe presentations and overuse of antibiotics. The emergence of the outbreak strain ribotype ARL 027 that produces more toxin and spores has been linked with more severe *C. difficile* disease and a greater chance of relapse. In addition, newer medications like the antibiotic fidaxomicin (Dificid) offer additional treatment options for *C. difficile* disease. In a study published by L. Kyne et al. 1999, the authors performed a detailed characterization of disease states for an outbreak of CDAD in Dublin, Ireland. This particular outbreak involved 14 patients that were stool cytotoxin positive but asymptomatic. Of the symptomatic patients, 25% had mild-self-limiting disease with no antibiotic treatment, 35% had moderately severe *C. difficile* disease responding to antibiotic treatment and 40% developed severe disease with prolonged symptoms lasting between eleven to thirty-six days. A total of 8% of the patients with *C. difficile* disease progressed to severe colitis with pseudomembranes and toxic megacolon. The authors noted that physicians should be aware of early indicators of disease severity in order to lower morbidity and mortality for cases of *C. difficile* disease.

A combination of clinical presentations and various lab parameters have been evaluated for stratifying patients by disease activity (e.g., mild, moderate, and moderate-to-severe). White blood cell count (WBC), serum albumin level (indicator of leakage into the bowel), and creatinine level for monitoring kidney failure are the most commonly used lab indicators for disease activity for *C. difficile*. Mild to moderate cases of *C. difficile* usually present with a WBC≤15,000/μL, normal serum creatinine (<2.0 mg/dL) and albumin levels (≥2.5 g/dL). Symptoms include having less than 10 watery stools without blood per day and mild cramping lasting for up to an average of 4 days. A common treatment for patients with an initial episode of mild to moderate *C. difficile* disease is treatment with a member of the nitroimidazole class of antibiotics. For example, mild to moderate *C. difficile* disease may be treated with 500 mg metronidazole, three times daily for ten days. Most cases resolve with no further complications, but up to 25% of these cases may relapse multiple times and require a second round of antibiotics, which historically has included treatment with a member of the glycopeptide class of antibiotics, such as vancomycin. However, now such second rounds of antibiotics include members of the macrocyclic class of antibiotics, such as fidaxomicin (Dificid).

Patients over the age of sixty-five with multiple co-morbidities are at a higher risk for *C. difficile* disease and more often suffer from more severe disease leading to multiple relapses. Severe fulminant *C. difficile* disease is characterized by having eleven or more liquid stools per day for more than ten days. Stool specimens often contain mucus and may be bloody. Defined lab parameters for fulminant *C. difficile* colitis are WBC≥15,000/μL, a rising serum creatinine (50% increase and levels≥2.0 mg/dL) indicating poor kidney function and albumin levels dropping below 2.5 g/dL showing loss of protein because of exudation of serum into the bowel. Clinical presentations may involve pseudomembranes on endoscopy, severe abdominal pain and cramping, and colonic thickening observed by CT scan. Toxic megacolon stemming from ileus may occur causing nausea, vomiting, severe dehydration, and extreme lethargy. Treatment for severe and relapsing cases of *C. difficile* disease usually involves 125 mg vancomycin 4 times per day for 10 days.

Identifying disease activity for patients with *C. difficile* infection is imperative for proper treatment and better outcome with decreased morbidity and mortality. An embodiment of the invention provides a diagnostic parameter for assessing severity in *C. difficile* disease by measuring fecal lactoferrin and using the measurement of fecal lactoferrin as an indicator for intestinal inflammation caused by *C. difficile*.

*C. difficile* disease is an inflammatory disease involving the infiltration of activated neutrophils across the mucosa into the lumen causing colitis and in severe cases, the formation of pseudomembranes. Human lactoferrin is a glycoprotein that is present in most mucosal secretions and a primary component of the granules of activated neutrophils. During the onset of intestinal inflammation from *C. difficile*, activated neutrophils infiltrate the intestinal lumen causing an increase in fecal lactoferrin.

Fecal specimens are routinely collected for *C. difficile* testing (antigen and toxin). Accordingly, additional testing can be done to measure the level of fecal lactoferrin for determining the amount of intestinal inflammation as an indicator of disease severity. In addition, combining the presence of antigen and the levels of toxins A and B with fecal lactoferrin concentrations can help the physician in determining if a patient is a carrier from patients that have true mild to severe infections for optimal medical treatment.

In an embodiment of the present invention, a method for assessing disease severity in patients with *C. difficile* disease using fecal lactoferrin levels is provided. Toxin A is a strong chemotactic protein that causes the release of IL-8 and the infiltration of activated neutrophils into the intestinal mucosa. In fact, toxin A concentrations of 100-fold less than that of toxin B have been shown to stimulate the release of IL-8. Toxin A also stimulates other pro-inflammatory cytokines including Il-1β and tumor necrosis factor alpha (TNF-α). Toxin B is a cytotoxin that causes tissue damage and inflammation that contributes, along with toxin A that causes fluid accumulation, to disease. The combined effects of the enterotoxic and chemotactic toxin A and cytotoxic effects of toxin B strongly contribute to the severity of disease. In a study by Kuehne et al., knockout mutants showed that both A+B− and A−B+ mutants were cytotoxic and caused disease in the hamster model. An interesting finding was that when tcdB was inactivated by an insertion, the resulting A+B− mutant showed increased cytotoxicity of toxin A in cell culture. The increased cytotoxicity was not neutralized completely by anti-toxin A specific antibody. The reason for the increase of cytotoxicity following the inactivation of tcdB was not determined but thought to be due to increased expression. The double knockout mutant A−B− did not cause disease in the hamster. These results confirmed that both TcdA and TcdB in combination and independently cause disease. In another study, the analysis of A−B+ isolates showed a variant toxin B that was significantly more lethal in a mouse than normal toxin B. These studies support the role of both toxins in the disease. A method for determining the presence of intestinal inflammation in combination with the presence toxin in stool can offer additional information on disease status for patients with *C. difficile* infection.

An embodiment of the present invention provides for determining the presence of *C. difficile* disease using a biomarker panel that includes, by way of example, *C. difficile* antigen (GDH), toxins A (tcdA or TcdA) and B (tcdB or TcdB) for determining the presence of toxigenic *C. difficile*. As will be understood, further embodiments of the invention utilize additional biomarkers for *C. difficile* infection. When a diagnosis of *C. difficile* disease is concluded, fecal lactoferrin concentrations may be used to determine disease severity. In patients suspected of infection with *C. difficile*, if GDH is present, indicating the presence of *C. difficile*, then toxins A and/or B (genes and/or protein) are detected to show the presence of toxigenic *C. difficile* followed by measuring fecal lactoferrin levels as an indicator of intestinal inflammation. Knowing whether toxigenic *C. difficile* is present in combination with a lactoferrin concentration will help to determine disease severity to optimize treatment.

In embodiments, serial measurements of biomarkers for *C. difficile* infection are utilized. For example, lactoferrin, GDH, toxin A, and/or toxin B levels may be monitored at regular intervals during analysis and/or treatment. In embodiments, serial analysis of the presence of one or more biomarkers (e.g. GDH, toxins A and/or B) provides an indicator of the bacteria, which may be used to determine a patient's response to treatment.

In embodiments, the level of lactoferrin in fecal samples provides an indication of the severity of *C. difficile*. For example, "mild" *C. difficile* disease may be indicated in samples with less than 7.25 μg/mL lactoferrin. In embodiments, a diagnosis of mild *C. difficile* disease is indicated in samples with less than 7.25 μg/mL lactoferrin, combined with clinical indicators for defining the mild disease. For example, clinical indicators such as the number of unformed stools per day, a presence of fever, abdominal pain, and vomiting may be characterized and/or determined as being indicative of a diagnosis of mild C. difficile disease, and may be analyzed together with a measurement of less than 7.25 µg/mL lactoferrin, to determine disease severity. In embodiments, clinical indicators for a diagnosis of mild C. difficile include having three to five stools per day and a white blood cell count less than or equal to 15,000/mm$^3$. In further embodiments, lab parameters such as C-reactive protein (CRP), white blood cell count (WBC), serum albumin, and/or creatinine, may be combined with a level of lactoferrin, a level of calprotectin, and/or a clinical indicator(s) to determine disease severity in patients diagnosed with mild C. difficile.

In another example, "moderate" C. difficile disease may be indicated in samples with between 7.25 µg/mL to 99.99 µg/mL lactoferrin. In some embodiments, a diagnosis of moderate C. difficile disease is indicated in samples with between 7.25 µg/mL to 99.99 µg/mL lactoferrin, combined with clinical indicators for defining the moderate disease. For example, clinical indicators such as the number of unformed stools per day, a presence of fever, abdominal pain, and vomiting may be characterized and/or determined as being indicative of a diagnosis of moderate C. difficile disease, and may be analyzed together with a measurement between 7.25 µg/mL to 99.99 µg/mL lactoferrin, to determine disease severity. In embodiments, clinical indicators for a diagnosis of moderate C. difficile include having six to nine stools per day, a white blood cell count from 15,001/mm$^3$ to 20,000/mm$^3$, and moderate abdominal pain. In further embodiments, lab parameters such as C-reactive protein (CRP), white blood cell count (WBC), serum albumin, and/or creatinine, may be combined with a level of lactoferrin, a level of calprotectin, and/or a clinical indicator(s) to determine disease severity in patients diagnosed with moderate C. difficile.

In a further example, "moderate-to-severe" C. difficile disease may be indicated in samples with 100 µg/mL or greater lactoferrin. In some embodiments, a diagnosis of moderate-to-severe C. difficile disease is indicated in samples with 100 µg/mL or greater lactoferrin, combined with clinical indicators for defining the moderate-to-severe disease. For example, clinical indicators such as the number of unformed stools per day, a presence of fever, abdominal pain, and vomiting may be characterized and/or determined as being indicative of a diagnosis of moderate-to-severe C. difficile disease, and may be analyzed together with a measurement of 100 µg/mL or greater lactoferrin, to determine disease severity. In embodiments, clinical indicators for a diagnosis of moderate-to-severe C. difficile include having ten or greater stools per day, a white blood cell count of 20,001/mm$^3$ or greater, and severe abdominal pain. In further embodiments, lab parameters such as C-reactive protein (CRP), white blood cell count (WBC), serum albumin, and/or creatinine, may be combined with a level of lactoferrin, a level of calprotectin, and/or a clinical indicator(s) to determine disease severity in patients diagnosed with moderate-to-severe C. difficile.

One exemplary method of testing for the presence of the C. difficile GDH biomarker is to use the C. DIFF CHEK™-60 test, which uses antibodies specific for C. difficile GDH. The Microassay Plate contains immobilized polyclonal antibody against the GDH antigen, while the Conjugate consists of a highly specific monoclonal antibody conjugated to horseradish peroxidase. If the GDH antigen is present in the specimen, a color is detected due to the enzyme-antibody-antigen complexes that form in the assay.

One exemplary method of testing for the presence of toxin A and toxin B is to use the C. DIFFICILE TOX A/B II™ test, which uses antibodies to C. difficile toxins A and B. The test utilizes immobilized affinity-purified polyclonal antibody against toxins A and B, and the detecting antibody consists of a mixture of toxin A monoclonal antibody conjugated to horseradish peroxidase and toxin B polyclonal antibody conjugated to horseradish peroxidase. If toxins A and B are present in the specimen, a color is detected due to the enzyme-antibody-antigen complexes that form in the assay.

One exemplary method of testing for the presence of GDH, toxin A and toxin B is to use the QUIK CHEK COMPLETE™ test, which uses antibodies specific for GDH and toxins A and B of C. difficile. The device contains three vertical lines of immobilized antibodies, the antigen test line contains antibodies against C. difficile GDH, and the control line is a dotted line that contains anti-horseradish peroxidase antibodies. The toxins A and B test line contains antibodies against C. difficile toxins A and B and the Conjugate consists of antibodies to GDH and antibodies to toxins A and B coupled to horseradish peroxidase. The GDH reaction is examined visually for the appearance of a vertical blue line, which indicates a positive test, while a blue line also indicates a positive test for toxin A and toxin B.

One exemplary method of testing for the presence of C. difficile toxin is the C. DIFFICILE TOX-B TEST™, which uses a tissue culture format to detect the presence of cytotoxic activity in fecal specimens and confirms the identification of C. difficile toxin us g specific antitoxin. The test confirms the presence of C. difficile toxin by neutralizing the cytotoxic activity with a reagent that is a specific antitoxin. In the assay, if C. difficile toxin is present, the cells in the well with PBS will become round, demonstrating the presence of the cytotoxic activity, while the presence of C. difficile toxin is confirmed if the cytotoxic activity is neutralized in the well containing antitoxin.

One exemplary method of treating C. difficile is through a native flora transplant. This process, also referred to as Fecal (or Faecal) Microbiota Transplantation (FMT), is the restoration of the colonic flora by introducing healthy bacterial flora through infusion of stool, e.g. by enema, obtained from a healthy human donor. A native flora transplant can also be administered as a liquid that the patient drinks.

The following are examples of procedures which have been utilized to establish the preferred assays according to the present invention. The following examples are merely exemplary and not presented by way of limitation.

EXAMPLE 1

Fecal lactoferrin levels were evaluated in patients with clinically defined C. difficile disease ranging from mild to moderate-to-severe disease. Briefly, patients with clinically confirmed C. difficile disease presenting with a spectrum of severity were recruited along with fourteen age-sex matched healthy subjects defined as having no intestinal illnesses. Disease activity was defined by physician's assessment and based on symptoms, serum albumin, WBC counts and co-morbidities. Fecal lactoferrin was measured using a quantitative enzyme immunoassay (EIA). C. difficile glutamate dehydrogenase (GDH) and toxins A and B in stool were detected using a membrane-based EIA. Toxigenic culture was done using spore enrichment and both isolates and stool specimens were tested by tissue culture assay for cytotoxicity.

Results

Thirty-nine clinically confirmed cases of C. difficile disease (fifteen moderate-to-severe, twenty-one moderate and three mild) were tested during a six month period. Ages ranged from thirty-two to eighty-nine years and fifty percent were female. The predominant co-morbidities were diabetes (31%), cancer (23%) and renal failure (23%). All patients were GDH-positive and toxigenic *C. difficile* was isolated from all but four patients. The mean lactoferrin levels (µg/mL±std error) were 1198±404 for moderate-to-severe, 132±50 for moderate, 12±5 for mild and 2±0.3 for healthy subjects. Stool toxin was detected by tissue culture in 87% (13/15) of moderate-to-severe, 71% (15/21) of moderate and 33% (1/3) for mild disease. Two of the moderate-to-severe patients with the lowest lactoferrin levels (≤8 µg/mL) and three of the four lowest with moderate (≤12 µg/mL) were also tissue culture-negative. Of these patients, both of the severe and two of the four moderate patients had negative stool cultures. All of these patients had co-morbidities that contributed to the clinical assessments. Our conclusion is that in a clinical setting, co-morbidities can complicate the clinical assessment for *C. difficile* infection. Our results show that fecal lactoferrin is useful for indicating disease severity in patients with *C. difficile* infection.

Accordingly, Table 1 below details the patient characteristics for clinically confirmed cases of *C. difficile* disease. Most patients were >64 years old, experienced pain, had liquid stools and suffered with co-morbidities including diabetes, cancer, renal failure and pneumonia. FIG. 1 shows that lactoferrin levels were significantly higher between mild, moderate, and moderate-to-severe cases of *C. difficile* disease, and trended higher for the moderate-to-severe group.

ferrin by enzyme-linked immunoassay (EIA). Specimen collection was initiated at the start of antibiotic treatment and was continued on a daily to weekly basis when possible. A symptom log was kept by each patient and all treatments were recorded during the test period. Both patients showed a rapid response to antibiotic treatment with fecal GDH, toxins A and B, and fecal lactoferrin reaching baseline within 24 hours. Antigen, toxin and fecal lactoferrin remained negative during the antibiotic therapy. Following the treatment, both patients experienced a clinical relapse and showed a rapid increase for all parameters. Following a second course of antibiotics, all parameters returned to baseline. At completion of the second course of antibiotics, all parameters increased rapidly in absence of clinical symptoms. Both GDH and toxin remained present for 3 to 4 weeks but fecal lactoferrin quickly returned to baseline. No antibiotics were administered since there were no clinical symptoms and patients remained healthy.

Results

In this evaluation, it was observed that *C. difficile* GDH, toxin and fecal lactoferrin levels responded quickly to antibiotic therapy by returning to baseline (negative). More interestingly, both GDH and toxin were present without clinical symptoms and with no intestinal inflammation as determined by baseline lactoferrin. These results show a role for fecal lactoferrin in combination with antigen and toxin measurements for determining which cases of *C. difficile* disease may require no further treatment with antibiotics. In

TABLE 1

Patient Characteristics for Clinically Confirmed Cases of *C. difficile* disease

| PATIENT CHARACTERISTICS | | PERCENT OF TOTAL N = 39 | PERCENT OF MOD-TO-SEVERE N = 15 | PERCENT OF MODERATE N = 21 | PERCENT OF MILD N = 3 |
|---|---|---|---|---|---|
| GENDER | MALE | 41 | 60 | 29 | 33 |
|  | FEMALE | 59 | 40 | 71 | 67 |
| AGE | <65 YR | 44 | 40 | 48 | 33 |
|  | >64 YR | 56 | 60 | 52 | 67 |
| PAIN | YES | 67 | 60 | 71 | 67 |
|  | NO | 33 | 40 | 29 | 33 |
| CO-MORBIDITIES | DIABETES | 30 | 13 | 29 | 33 |
|  | CANCER | 23 | 13 | 29 | 33 |
|  | RENAL FAILURE | 23 | 20 | 29 | 33 |
|  | PNEUMONIA | 18 | 27 | 10 | 0 |
| STOOL CONSISTENCY | SOLID | 3 | 0 | 5 | 0 |
|  | SEMI-SOLID | 44 | 33 | 43 | 100 |
|  | LIQUID | 54 | 67 | 52 | 0 |
| CLINICAL ASSESSMENT | SEVERE | 38 | 100 | 0 | 0 |
|  | MODERATE | 54 | 0 | 100 | 0 |
|  | MILD | 8 | 0 | 0 | 100 |

Figure 2:
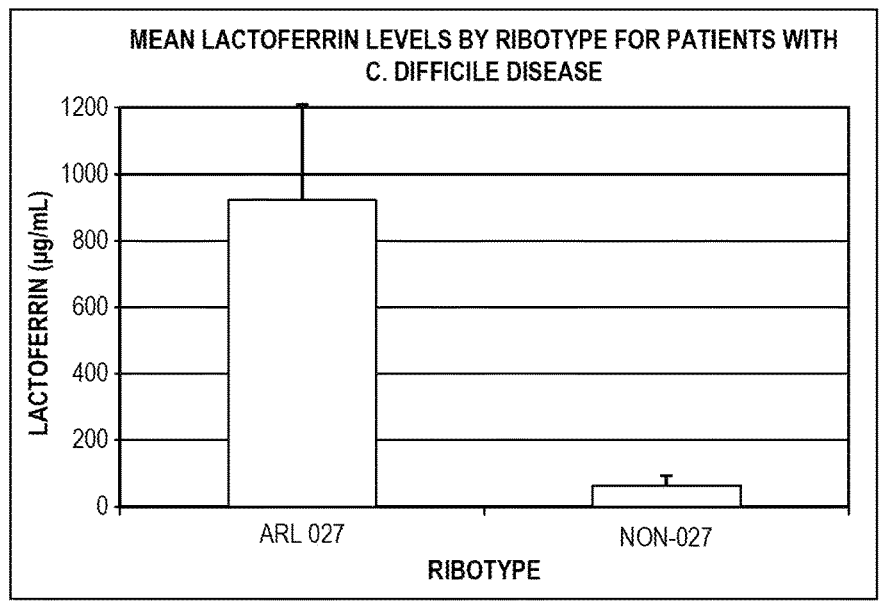
FIG. 2 depicts mean lactoferrin levels (μg/mL±standard error) for patients having ribotype ARL 027 *C. difficile* infection (denoted ARL 027) versus patients having other ribotype *C. difficile* infections (denoted NON-027) according to embodiments of the invention.

FIG. 2 shows the mean lactoferrin levels for patients with clinically confirmed *C. difficile* disease grouped by ribotype. Patients infected with ARL 027 had significantly higher levels of lactoferrin than patients infected with other ribotypes. Studies have shown that patients infected with ARL 027 tend to have stool toxin and present with more severe disease.

EXAMPLE 2

Fecal *C. difficile* GDH, toxins A and B, and human lactoferrin levels were measured in several subjects with *C. difficile* disease during antibiotic treatment. Both subjects with clinically confirmed *C. difficile* disease were monitored for the presence of GDH, toxins A and B and fecal lactoaddition, our invention provides a role for fecal lactoferrin in monitoring *C. difficile* disease. By determining the amount of intestinal inflammation using lactoferrin in *C. difficile* disease patients along with clinical assessments, the identification of patients for severity of disease may prove useful for optimizing treatment and leading to better patient outcomes.

Treatment may be optimized for *C. difficile* disease since varying levels of severity call for different treatment recommendations. For example, mild cases of *C. difficile* disease often receive no antibiotic treatment. In contrast, a case of moderate severity may call for an antibiotic such as metronidazole while a moderate-to-severe case of *C. difficile* disease may be treated with antibiotics such as vancomycin and fidaxomicin (Dificid).

Figure 3:
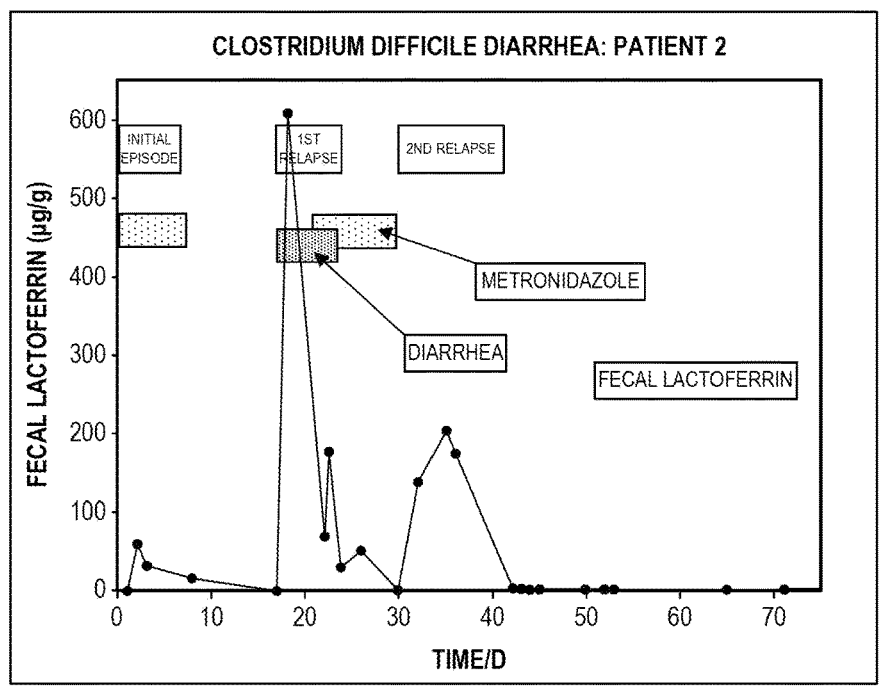
FIG. 3 depicts a graph of fecal lactoferrin levels in μg/g over time in days (denoted TIME/D) during and after antibiotic treatment in a patient with *C. difficile* disease according to embodiments of the invention.

FIG. 3 illustrates daily lactoferrin levels from the initial episode of *C. difficile* infection, during, and after antibiotic treatment. Lactoferrin was elevated (≥7.25 μg/mL) during the initial episode and for both periods of relapse. Levels drop rapidly once treatment is started and increased as symptoms return.

EXAMPLE 3

Patients (pts) with diarrhea and positive stool toxin (TcdA and TcdB) and/or glutamate dehydrogenase (GDH) were recruited with Informed Consent. Stool specimens were collected starting at admission (T=0) to Follow-up (T=F). GDH, toxin, and lactoferrin (LF: median μg/g) were measured in stool specimens by immunoassay. Bacterial culture and counts (median CFU#/g) were done using ethanol enrichment and isolates were ribotyped. A total of 18 inpatients were recruited and followed for a median period of 21 days from T=0 to T=F. Median age was 75 yr and the male:female ratio was 1:3.5. Pts were stratified into 3 groups (i) pts who were treated and showed no recurrence (N=9). (ii) pts who were treated with complete resolution of symptoms but had CDI (N=5) and (iii) pts that responded initially to treatment but relapsed (N=4).

Results

Patients in group (i) went from strongly positive for GDH, toxin and a spore count of $10^4$ at T=0 to negative for all biomarkers at T=F. LF fell from 406 to 4 during this period (FIG. 4A). Four of the 5 pts in group (ii) were positive for GDH, toxin, and had a spore count of $10^4$ at T=0. At T=F, 3 of the 5 pts were toxin negative, 3 pts remained GDH-positive and all pts had spores ($10^3$). LF for these pts dropped from 85 to 2 associated with resolution of symptoms (FIG. 4B). For group (iii), all 4 pts remained symptomatic and stayed strongly positive for GDH, toxin, and had a spore count of $10^4$. LF levels for this group were similar at both T=0 and T=F (362 and 315, respectively) (FIG. 4). A total of 5 (28%) pts had 027 CDI at T=0. In group (ii), 3 of 5 pts were reinfected with 027 as carriers. In group (iii), 1 patient converted to 027. **All of the 027 isolates were fluoroquinolone resistant. In our study, at T=F 50% of pts had no CDI, 28% became carriers and 22% remained ill. GDH, toxin and LF levels all correlated with the presence of clinical disease. *C. difficile* continues to be a complex infection, and accurate diagnosis of disease relies on the clinical history used in conjunction with biomarkers for the organism and for inflammation.

FIG. 4A shows the results of CDI biomarkers before and after antibiotic treatment for *C. difficile* disease. All of the patients in this group had a clinical cure meaning no symptoms and no *C. difficile* detected during and after initial antibiotic treatment.

FIG. 4B shows the results of CDI biomarkers before and after antibiotic treatment for *C. difficile* disease. All patients in this group had a reinfection of *C. difficile* meaning that the *C. difficile* organism was detected in absence of symptoms during and/or after initial antibiotic treatment.

FIG. 4C shows the results of CDI biomarkers before and after antibiotic treatment for *C. difficile* disease. All patients in this group had a clinical recurrence or no cure meaning that symptoms and the *C. difficile* organism was maintained or returned during and/or after initial antibiotic treatment.

In an alternative embodiment, fecal calprotectin may be utilized rather than, or in addition to, fecal lactoferrin as a non-invasive marker for measuring intestinal inflammation. For example, in a person diagnosed with *C. difficile* disease, a quantitative level of fecal calprotectin may be measured and the quantitative level may be associated with a disease severity including mild, moderate, and moderate-to-severe. Further, fecal calprotectin may be measured subsequent to treatment to monitor a person's response to medical treatment or an activity level of the disease.

In summary, the present invention is directed to non-invasive methods for identifying a severity of *C. difficile* disease in persons diagnosed with *C. difficile* disease using lactoferrin. The identified disease severity may be used to recommend a preferred course of treatment for the person. The present invention is further directed to utilizing changes in lactoferrin levels to monitor a person's disease activity and/or response to treatment.

The immunoassays of the present invention detect lactoferrin, a stable protein that serves as an indicator of intestinal inflammation, and provide quantitative fecal lactoferrin levels for associating a disease severity to *C. difficile* disease and for monitoring disease activity. The present invention has been described in relation to particular embodiments which are intended in all respects to be illustrative rather than restrictive. Alternative embodiments will become apparent to those skilled in the art to which the present invention pertains without departing from its scope.

From the foregoing, it will be seen that this invention is one well adapted to attain all the ends and objects herein above set forth together with other advantages which are obvious and which are inherent to the method. It will be understood that certain features and subcombinations are of utility and may be employed without reference to other features and subcombinations. This is contemplated by and is within the scope of the claims.

What the invention claimed is:

1. A method of treating a patient with a *C. difficile* infection, the method comprising:
   quantitatively measuring a level of lactoferrin in a fecal sample from a patient with a *C. difficile* infection;
   determining that the patient has moderate-to-severe *C. difficile* disease based on the measured level of lactoferrin in the fecal sample being equal to or greater than 100 μg/mL; and
   subsequent to the determining that the patient has moderate-to severe *C. difficile* disease, administering a therapeutically effective treatment, the therapeutically effective treatment comprising a native flora transplant.

2. The method of claim 1, wherein the level of lactoferrin in the fecal sample is determined via a quantitative enzyme immunoassay (EIA).

3. The method of claim 1, further comprising: subsequent to administering the therapeutically effective treatment for *C. difficile* disease, determining a presence of one or more biomarkers to indicate the presence or absence of *C. difficile* bacteria in the patient.

4. The method of claim 3, wherein the one or more biomarkers comprises *C. difficile* toxin A or *C. difficile* toxin B.

5. A method of treating a patient with *C. difficile* disease, the method comprising:
   obtaining a fecal sample from a patient having been diagnosed with *C. difficile* disease;
   measuring the fecal sample for a level of lactoferrin; and
   determining that the patient has moderate-to-severe disease based on the measured fecal sample having a level of lactoferrin equal to or greater than 100 μg/mL; and subsequent to the determining that the patient has moderate-to severe *C. difficile* disease, administering a therapeutically effective treatment comprising a native flora transplant.

6. The method of claim 5, wherein the level of lactoferrin in the fecal sample is determined via a quantitative enzyme immunoassay (EIA).

7. The method of claim 5, wherein the determining the patient has moderate-to-severe *C. difficile* disease is further based on one or more of:
   clinical indicators of the patient, the clinical indicators comprising one or more of a number of unformed stools per day, a presence of fever, abdominal pain, and vomiting; and
   lab tests of the patient, the lab tests comprising one or more tests for C-reactive protein (CRP), white blood cell count (WBC), serum albumin, and creatinine.

8. The method of claim 5, wherein the patient having been diagnosed with *C. difficile* disease was diagnosed at least partly by detecting a presence of a biomarker that indicates a presence of toxigenic *C. difficile*.

\* \* \* \* \*